United States Patent
Kuehn et al.

(10) Patent No.: US 12,023,184 B2
(45) Date of Patent: Jul. 2, 2024

(54) GANTRY FRAME FOR A COMPUTED TOMOGRAPHY SYSTEM

(71) Applicant: Siemens Healthcare GmbH, Erlangen (DE)

(72) Inventors: Ulrich Kuehn, Baiersdorf (DE); Matthias Hupfauf, Nabburg (DE)

(73) Assignee: Siemens Healthineers AG, Forchheim (DE)

( * ) Notice: Subject to any disclaimer, the term of this patent is extended or adjusted under 35 U.S.C. 154(b) by 219 days.

(21) Appl. No.: 17/589,978

(22) Filed: Feb. 1, 2022

(65) Prior Publication Data

US 2022/0249034 A1    Aug. 11, 2022

(30) Foreign Application Priority Data

Feb. 8, 2021   (DE) ................. 10 2021 201 160.8

(51) Int. Cl.
*A61B 6/03* (2006.01)
*A61B 6/00* (2024.01)
*H05G 1/04* (2006.01)

(52) U.S. Cl.
CPC .......... *A61B 6/035* (2013.01); *A61B 6/4435* (2013.01); *A61B 6/4452* (2013.01); *A61B 6/54* (2013.01); *H05G 1/04* (2013.01)

(58) Field of Classification Search
CPC ..... A61B 6/035; A61B 6/4435; A61B 6/4447; A61B 6/4429; A61B 6/44; A61B 6/4411; H05G 1/02
See application file for complete search history.

(56) References Cited

U.S. PATENT DOCUMENTS

| | | | | |
|---|---|---|---|---|
| 6,314,157 | B1* | 11/2001 | Tachizaki | A61B 6/035 378/197 |
| 7,020,233 | B1* | 3/2006 | Tybinkowski | A61B 6/4417 250/363.04 |
| 9,668,330 | B2* | 5/2017 | Matsuzawa | G01N 23/046 |
| 10,918,345 | B2* | 2/2021 | Knox | F16C 13/04 |
| 2001/0055362 | A1* | 12/2001 | Takanashi | G01N 23/046 378/4 |
| 2007/0064863 | A1* | 3/2007 | Buttner | G01N 23/046 378/4 |
| 2010/0025590 | A1* | 2/2010 | Luecke | A61B 6/035 250/363.05 |
| 2010/0027759 | A1* | 2/2010 | Luecke | A61B 6/4429 378/197 |
| 2010/0266105 | A1* | 10/2010 | Sharpless | A61B 6/035 378/198 |
| 2011/0316538 | A1* | 12/2011 | Kim | A61B 6/4435 324/318 |

(Continued)

FOREIGN PATENT DOCUMENTS

DE   102013205606 A1   10/2014

*Primary Examiner* — Dani Fox
*Assistant Examiner* — Soorena Kefayati
(74) *Attorney, Agent, or Firm* — Harness, Dickey & Pierce, P.L.C.

(57) ABSTRACT

A gantry frame for a computed tomography system is described. The gantry frame comprises a cylindrical drum frame with a cylinder barrel which has a profiled barrel structure. A gantry is also described. Additionally, a computed tomography system is described. A method for manufacturing a gantry frame for a computed tomography system is also described.

17 Claims, 9 Drawing Sheets

(56) References Cited

U.S. PATENT DOCUMENTS

| | | | |
|---|---|---|---|
| 2012/0027163 A1* | 2/2012 | Mochitate | A61B 6/4071 378/15 |
| 2012/0241393 A1* | 9/2012 | Roth | A61B 6/035 211/26 |
| 2013/0077737 A1* | 3/2013 | Fasoli | G01N 23/04 378/4 |
| 2014/0016758 A1* | 1/2014 | Theiss | A61B 6/035 378/197 |
| 2014/0205059 A1* | 7/2014 | Sharpless | A61B 6/4429 378/17 |
| 2014/0270051 A1* | 9/2014 | Smithanik | A61B 6/4435 378/197 |
| 2015/0164448 A1* | 6/2015 | Liu | A61B 6/037 600/407 |
| 2015/0216492 A1* | 8/2015 | Smith | A61B 6/44 378/208 |
| 2015/0265229 A1* | 9/2015 | Maki | A61B 6/032 378/197 |
| 2015/0265230 A1* | 9/2015 | Matsuzawa | A61B 6/44 378/197 |
| 2016/0058398 A1* | 3/2016 | Jensch | A61B 6/035 378/204 |
| 2017/0042008 A1* | 2/2017 | Hills | G01V 5/226 |
| 2017/0237217 A1* | 8/2017 | Moore | A61B 6/56 439/19 |
| 2017/0238889 A1* | 8/2017 | Murch | A61B 6/56 |
| 2017/0258428 A1* | 9/2017 | Distler | A61B 6/035 |
| 2017/0281105 A1* | 10/2017 | Basu | A61B 6/4435 |
| 2017/0325764 A1* | 11/2017 | Yun | A61B 6/4435 |
| 2019/0111285 A1* | 4/2019 | Zheng | A61N 5/1081 |
| 2021/0138270 A1* | 5/2021 | Hale | A61B 6/4435 |

* cited by examiner

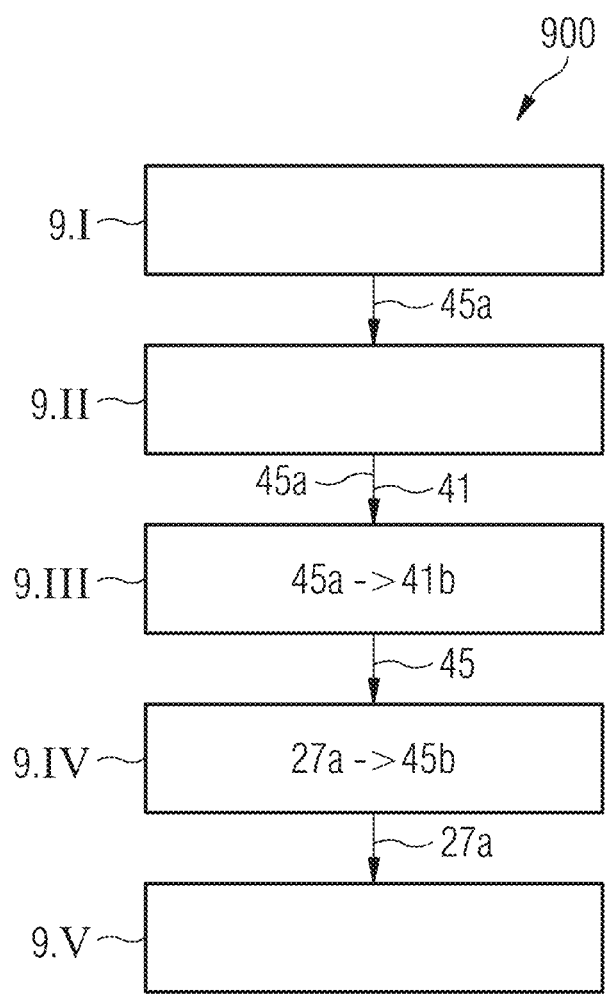

GANTRY FRAME FOR A COMPUTED TOMOGRAPHY SYSTEM

CROSS-REFERENCE TO RELATED APPLICATION(S)

The present application claims priority under 35 U.S.C. § 119 to German Patent Application No. DE 10 2021 201 160.8, filed Feb. 8, 2021, the entire contents of which are hereby incorporated herein by reference.

FIELD

One or more embodiments of the invention relate to a gantry frame for a computed tomography system. Furthermore, one or more embodiments of the invention relate to a gantry. One or more embodiments of the invention further relate to a computed tomography system. One or more embodiments of the invention additionally relate to a method for manufacturing a gantry frame for a computed tomography system.

BACKGROUND

With the help of modern imaging methods, two-dimensional or three-dimensional image data is frequently generated which can be used for the visualization of a patient to be mapped, for example a person or an animal, and additionally also for further applications.

SUMMARY

One or more embodiments of the invention specify a gantry frame for a computed tomography system and/or a method for manufacturing a gantry frame with an improved machinability of the gantry frame and simultaneously reduced and/or as low as possible manufacturing costs for the gantry frame.

One or more embodiments are achieved by a gantry frame for a computed tomography system, a gantry, a computed tomography system and/or a method for manufacturing a gantry frame for a computed tomography system.

A gantry frame for a computed tomography system, according to one or more embodiments, comprises a cylindrical drum frame with a cylinder barrel which has a profiled barrel structure. The drum frame serves to provide a front end surface as an attachment surface for retainers in front of the rotating part of a gantry.

A profile of a barrel structure should be understood as a location-dependent variation of the distance of the cylinder barrel from an internal and/or external sleeve cylinder, the longitudinal axis of which coincides with the longitudinal axis of the cylinder barrel. In this case the internal sleeve cylinder touches the cylinder barrel from the inside and the external sleeve cylinder touches the cylinder barrel from the outside in each case at at least one point on the internal surface or external surface of the cylinder barrel, wherein there is at least one area of the internal surface and/or of the external surface of the cylinder barrel which does not touch the respective sleeve cylinder. The profiles thus penetrate the ideal cylindrical shape of the cylinder barrel, wherein apart from the variation or the profile structure the cylindrical shape of the cylinder barrel is however essentially retained. If the cylinder barrel comprises multiple walls, an analogous definition applies, with a correspondingly increased number of sleeve cylinders.

The variation in the distance of the cylinder barrel is preferably effected in the circumferential direction or as a function of an azimuth of a position on the cylinder barrel.

The profiled barrel structure of the cylinder barrel of the cylindrical drum frame has the advantage that it is mechanically particularly stable. Consequently the drum frame of the gantry frame, according to one or more embodiments, is less deformed during the machining thereof, such that the drum frame of the gantry frame can be machined more precisely. For example, assembly sections, such as for example a machinable surface for the receipt of a retainer or a fastening element for a retainer, are generated on the drum frame by milling out. During this milling out an exact position of the retainers is established. Therefore the drum frame must not deform to a relevant extent during this work step, since if it did the machining positions on the drum frame would deviate from the predetermined exact position, such that the precision of the machining would suffer as a result.

The gantry, according to one or more embodiments, has a gantry frame, an imaging system, also referred to as a rotating part, with a rotatable drum and one or more X-ray sources mounted on the drum, one or more X-ray detectors mounted on the drum, and auxiliary units, also referred to generally as rotating components. The gantry shares the advantages of the gantry frame.

The computed tomography system, according to one or more embodiments, comprises an gantry. Part of the computed tomography system is also a control unit to control the gantry for a recording of X-ray raw data in accordance with an image recording protocol and an operating unit for entering control data for the control of an imaging procedure and for monitoring the imaging procedure. The computed tomography system shares the advantages of the gantry frame.

In accordance with the method for manufacturing a gantry frame for a computed tomography system, according to one or more embodiments, a cylindrical drum frame with a cylinder barrel is formed, which has a profiled barrel structure. The method for manufacturing a gantry frame for a computed tomography system shares the advantages of the gantry frame.

Further particularly advantageous embodiments and developments emerge from the following description and the figures, wherein the independent claims in one claim category can also be developed analogously to the dependent claims in a different claim category.

The profiled barrel structure preferably has a trapezoidal profile. The trapezoidal profile advantageously achieves an increased stability of the cylinder barrel of the drum frame of the gantry frame with little use of material, as a result of which a lower weight is achieved. The trapezoidal profile is advantageously formed in the axial direction, i.e. viewed in the direction of the longitudinal axis of the drum frame, wherein the trapezoidal surfaces of the trapezoids of the trapezoidal profile are oriented in parallel to the longitudinal axis of the drum frame. In other words, a normal to the trapezoidal surfaces runs parallel to the longitudinal axis. Hence where appropriate the radial dimensions, in other words the thickness of the cylinder barrel, can be reduced in comparison with conventional gantry frames with conventional hollow chamber structures. As already mentioned, with the increased stability the machinability of the gantry frame improves in comparison with conventional gantry frames. A trapezoidal profile can also be manufactured relatively easily with simple tools in comparison with other profiled, possibly more complex profile structures, as is explained below.

Likewise the cylinder barrel of the gantry frame preferably has a plurality of barrel sections, of which at least one barrel section, preferably a plurality of the barrel sections, comprises or comprise a profiled structure, preferably a trapezoidal profile, particularly preferably a double trapezoid profile. The more profiled barrel sections the barrel structure has in the circumferential direction, the greater the stability of the barrel structure because of the mechanical support effect of the profiled barrel structure. The particular advantages of a double trapezoid profile, in particular for a manufacturing process of a gantry frame, are explained fully below.

Very particularly preferably, each of the barrel sections actually has a profiled structure, preferably a trapezoidal profile and very particularly preferably a double trapezoid profile, which is concomitant with an even further improved stability of the barrel structure.

Likewise preferably, adjacent barrel sections are designed to be oriented virtually contrariwise. "Oriented virtually contrariwise" is here intended to mean that the adjacent barrel sections are approximately mirrored or are arranged rotated to one another by somewhat less or somewhat more than 180°, wherein the aforementioned deviation depends on the size of the circumference of the cylinder barrel and the extension of the individual barrel sections in the circumferential direction. In the case of a barrel section with an individual trapezoidal profile this means that the base of a trapezoidal profile and the roof side of a trapezoidal profile of adjacent barrel sections of the axis of rotation of the cylinder barrel are alternately facing one another, or the base of a trapezoidal profile of a barrel section is not so far away from this axis as the corresponding side of the trapezoidal profile of an adjacent barrel section. If the individual barrel sections each have an individual trapezoidal profile, then in the event that at least two types of barrel sections with at least one different base angle of the trapezoidal profile are selected, the barrel sections are assembled to form a cylinder barrel with a polygonal, approximately circular cross-section.

The profiles of all barrel sections of the drum frame of the gantry frame are however particularly preferably shaped identically. In this case the profile of the individual barrel sections must be designed such that their cross-sections form a circular arc after the individual barrel sections have been assembled. The barrel sections can advantageously be manufactured with an identical shape in each case with a single forming tool, as a result of which the cost of manufacturing is reduced in comparison with the manufacture of differently shaped barrel sections, for example using different forming tools.

If the individual barrel sections have an identical trapezoidal profile, the barrel sections can, as already mentioned, very particularly advantageously have a double trapezoid profile with two different (individual) trapezoidal profiles arranged so as to be oriented virtually contrarily to one another. In this case the base of a first trapezoid lies closer to the axis of rotation than the base of the second trapezoid. Furthermore, both the different trapezoidal profiles must have a different base angle, so that when the barrel sections are joined together a cylinder barrel with an approximately circular cross-section is produced. A single forming tool, such as for example a press mold or a casting mold, can advantageously be used for these shingle-like barrel sections, in order to manufacture all barrel sections, such that the outlay for manufacturing the barrel sections is reduced in comparison with manufacturing different barrel sections. Compared to manufacturing differently shaped barrel sections, the number of work processes for manufacturing the barrel sections needed for the drum frame is cut by half. The outlay when joining the individual barrel sections to form a cylinder barrel is also reduced by half because of the double cross-section width of the barrel sections in comparison with barrel sections with individual profiles of equal size.

The aforementioned variant is then advantageous in particular when the barrel sections of the cylinder barrel of the gantry frame are initially designed as individual separate barrel elements which are designed to be permanently connectable to one another using a joining technique. Individual barrel elements can then advantageously be more easily prefabricated and assembled subsequently, which for example simplifies a process based on the division of labor and reduces the space requirements for part of the manufacturing process.

The gantry frame described can be employed for a single-source CT system or a multi-source CT system. If it is used for a single-source CT system, the drum frame is arranged on one side on a supporting carrier structure, wherein the drum frame with the supporting carrier structure forms the gantry frame.

If the gantry frame is employed for what is known as a dual-source CT system or even a multi-source system in which the imaging system comprises two separate X-ray sources as well as two separate X-ray detectors opposite the respective X-ray sources and also additional auxiliary units or rotating components, the drum frame of the gantry frame has two cylindrical drum frame sections, which are referred to for short below as the first and second drum frame section. Both the drum frame sections each comprise a cylinder barrel, each of which has a profiled barrel structure. Because of the profiled barrel structure of both the cylinder barrels, both drum frame sections of the gantry frame are stabilized.

Both the drum frame sections additionally comprise two end surfaces in each case, an external and an internal end surface, of which in each case the internal end surface is connected to an end surface of a supporting carrier structure of the gantry frame arranged between both the drum frame sections. The external end surface of both the drum frame sections is in contrast oriented outward, in other words facing away from the supporting carrier structure. The carrier structure forms the supporting central element of the gantry frame, absorbs forces onto the gantry frame and stabilizes the entire gantry. The carrier structure preferably has a box profile. Thanks to the formation of a box profile the carrier structure becomes stable and in comparison with a solid construction the weight of the carrier structure is reduced and material is saved.

At least some of the additional auxiliary units or rotating components can advantageously be accommodated in a second drum, which is surrounded by the second drum frame section, if there is no space for it in a first drum, which is surrounded by the first drum frame section, since a larger number of units has to be accommodated there than in the case of a single-source CT system.

In this advantageous embodiment both the drums received by the drum frame extend the gantry preferably in an axial direction beyond the carrier structure in comparison with a single-source CT system, wherein the second drum is formed on the rear side of the carrier structure. In this way additional capacities for auxiliary units of a dual-source system or multi-source system are created, without increasing the clearance profile of the gantry frame, such that transportation through constricted openings, such as door frames or portals for example, is facilitated.

The drum frame or at least one of the cylindrical drum frame sections of the gantry frame preferably has a machined surface and/or a fastening element for the receipt of a retainer for extension elements at its external end surface, which faces away from the carrier structure. The extension elements serve among other things to enable a user or an operator of such a gantry to operate the associated computed tomography system with ease or to provide easy access to the operation. Peripheral units of the gantry of the gantry frame can advantageously be connected to the drum frame or the drum frame section and can be arranged and positioned particularly accurately on the end face of the gantry frame because of the increased precision of the structures of the machined surface or of the fastening element.

The extension elements of the gantry frame preferably have at least one of the following elements:
a control panel,
a display,
a protective enclosure,
a front cover,
a laser.

The precision of the arrangement of the retainers is particularly important, since functional units that are mounted on the retainers are allotted an accurate positioning in order to function correctly. For example, a laser is required in order to produce a fixed reference to the scanning plane when recording an image of a patient and to establish a scanning area. In the case of a biopsy, positions are established by a laser. It is crucial here for the health of a patient and the success of the biopsy that the desired body position is hit accurately. The positioning of a cover, also called a front cover, must also be precise, so that the cover is tight and for example none of the patient's bodily fluids can flow into the interior of the gantry. When closed, the front cover must also adopt a particularly precise position, so that it can be automatically determined whether the front cover is closed or open.

Particularly preferably the profiled barrel structure has a single-wall barrel structure. The barrel structure is advantageously simpler in structure in comparison with multi-wall barrel structures, for example barrel structures with hollow chamber structures, requires less material and weighs less. A gantry frame with a single-wall barrel structure is also easier to assemble and manufacture in comparison with a gantry frame with a hollow chamber structure, this being described more fully below in connection with a variant of the manufacturing method of the gantry frame.

Additional advantages emerge in particular with this particularly preferred variant of the method, in which individual barrel sections are initially formed as separate elements. This procedure can for example take place by a forming method, such as for example a pressing method or a stamping method, in which the individual barrel sections are formed from pre-cut metal sheets. By pressing the metal sheets, the barrel sections attain the desired profiled structure. The metal sheets can for example comprise steel as a material.

The prefabricated individual barrel sections are then connected to an end surface of a carrier structure. In this case they can for example be welded to the end surface of the carrier structure. For this procedure the individual barrel sections are positioned and oriented to one another and preferably joined to one another or joined into one another in a shingle-like or overlapping manner and preferably also welded, such that they form the cylinder barrel of the drum frame. The barrel sections can advantageously be initially prefabricated in a space-saving manner using simple tools and later assembled at the location of the final installation of the gantry frame.

If the profiled barrel structure is designed as a single-wall barrel structure, work steps for the manufacture of the gantry frame can advantageously be saved, in particular in comparison with the manufacture of a gantry frame with a hollow chamber structure. For example, the accessibility of the welding points is improved in comparison with a hollow chamber structure when the barrel sections are fastened to the carrier structure by welding. Then, in contrast to the fastening of barrel sections with hollow chamber structures, a welding device need be applied only from one side, for example from outside, when single-wall barrel sections are used, such that the installation of the barrel sections on the carrier structure is simplified.

Fastening elements can then be attached to one or more end surfaces of barrel sections fastened to the carrier structure in this way, or retainers can be attached directly. To this end the external end surfaces of the barrel sections in question can be appropriately pretreated. For example, recesses or projections can be formed in the external end surfaces, to which the fastening elements or retainers can then be attached. In an additional machining step the fastening elements can then be machined, preferably milled, such that they attain their final shape and are prepared for the receipt of retainers in the correct position for the previously mentioned extension elements.

BRIEF DESCRIPTION OF THE DRAWINGS

Embodiments of the invention are explained once again in greater detail below using example embodiments with reference to the attached figures. In this case the same components are provided with identical reference characters in the various figures, in which:

FIG. 9 shows a flow diagram which illustrates a method for manufacturing a gantry frame in accordance with an exemplary embodiment of the invention.

DETAILED DESCRIPTION

Figure 1:
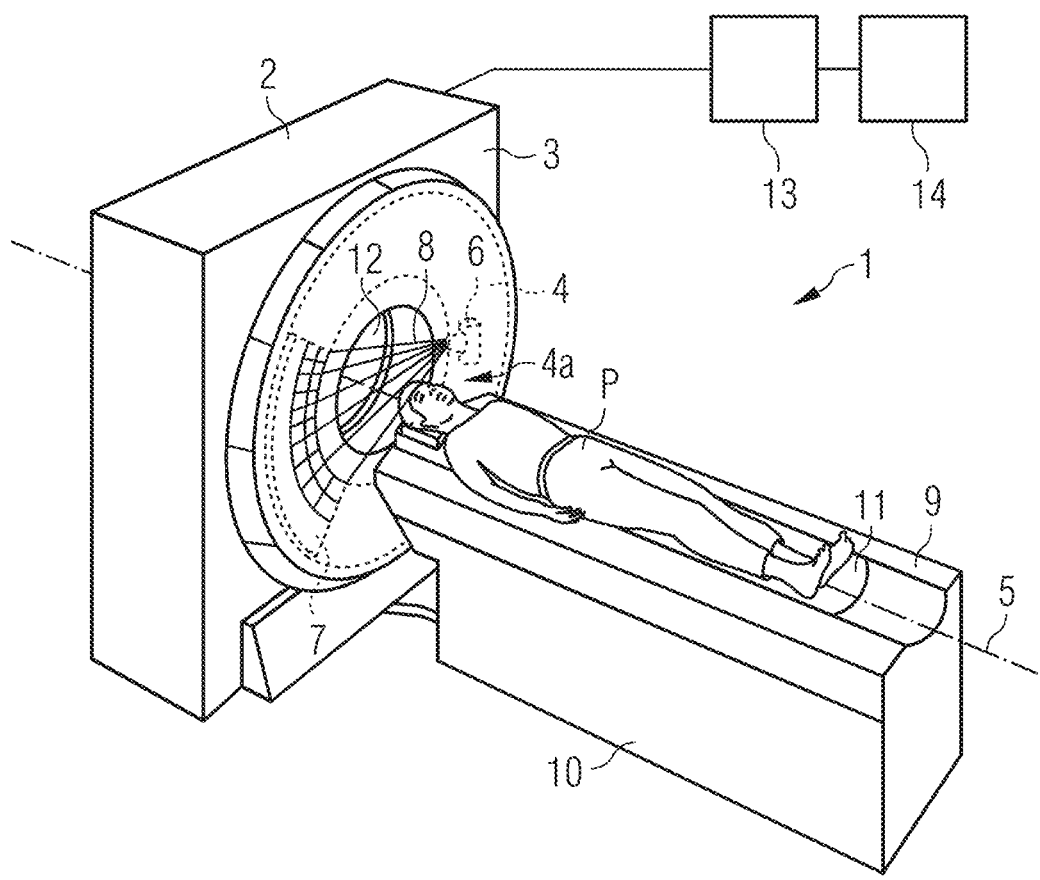
FIG. 1 shows a schematic representation of a computed tomography system in accordance with the conventional art.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one example embodiment, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A specific type of medical imaging is achieved by computed tomography. Computed tomography should be understood in the present patent application as all types of imaging methods in which a plurality of two-dimensional recordings, in particular image recordings, of an examination area captured from different directions is generated, on the basis of which a reconstruction of a sectional image is then carried out by a computer-based evaluation. For example, the term computed tomography includes what is known as transmission computed tomography, which in turn includes X-ray computed tomography based on the emission and detection of X-rays, which is particularly widely used in medicine.

As already mentioned, three-dimensional slice images of the interior of an object under examination are generated in computed tomography systems, also called CT systems for short, with the help of a two-dimensional image detection method. In the case of X-ray computed tomography, which in common parlance is also referred to for short as computed tomography, two-dimensional X-ray sectional images are generated for this purpose via an imaging system which comprises a drum generally rotating about the object to be recorded, an X-ray source fastened thereto and an X-ray detector likewise fastened to the drum and rotating with it, on the basis of which a volume calculation (image) is determined. The functional elements mentioned are mounted such that they can rotate about a system axis in a gantry housing, also referred to as a gantry frame, said gantry housing being arranged annularly around a recording space for the object under examination. The overall arrangement comprising the imaging system or the rotating part, the bearing and the gantry housing is referred to below as the gantry. FIG. 1 shows a general schematic representation of a computed tomography system, in order to elucidate its general structure.

The imaging system comprises the X-ray source and the X-ray detector designed to detect X-rays, as well as the control systems thereof, which are arranged in the gantry, as well as a drum-like apparatus called a drum, wherein the drum is moved in rotations about the system axis, in order to obtain X-ray recordings of the object being recorded from all directions. Located in the interior of the gantry is an annular protective cover with a central opening which expands outward in the shape of a funnel.

Figure 2:
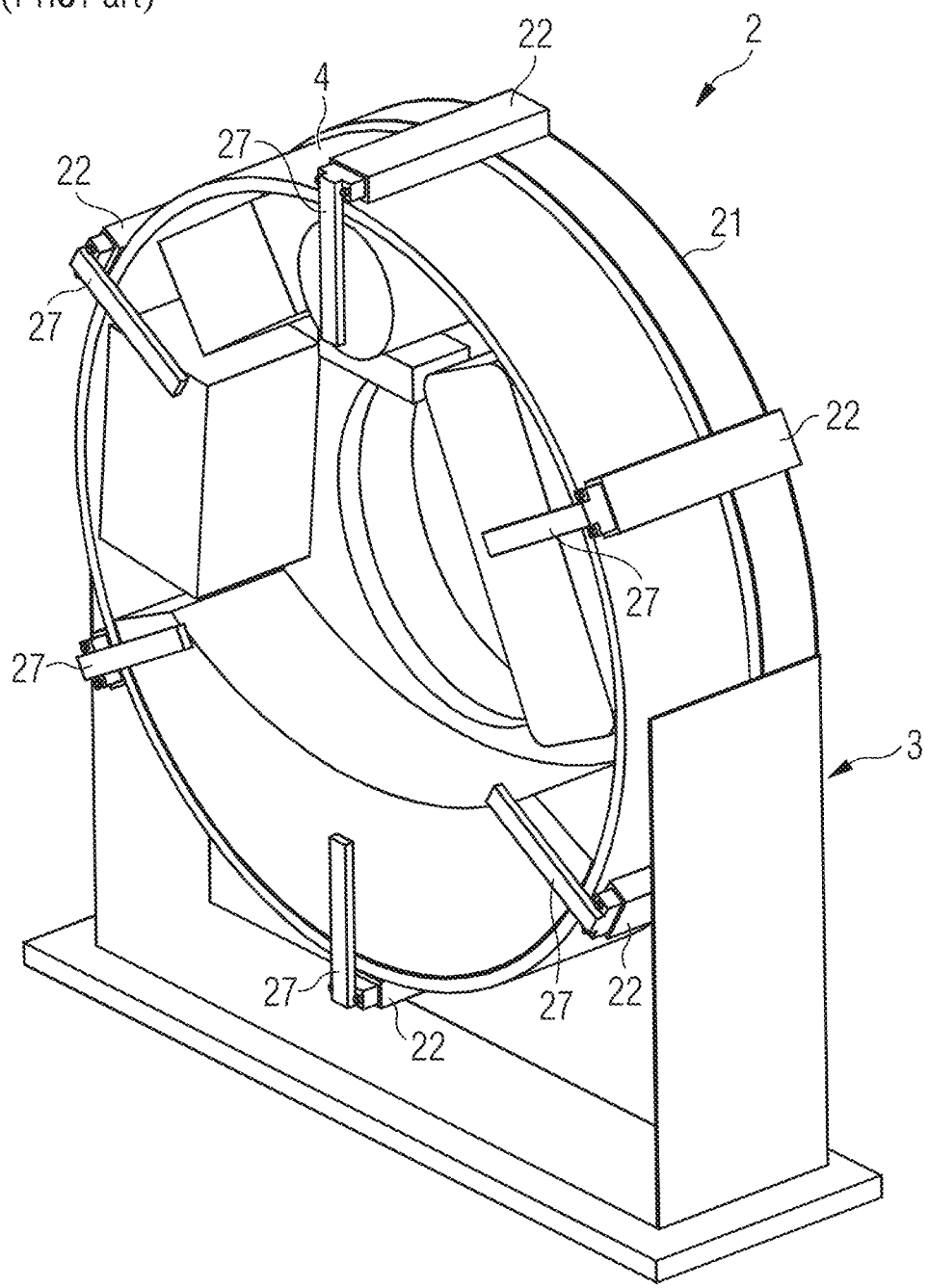
FIG. 2 shows a schematic representation of a gantry with a gantry frame with support arms in accordance with the prior art.

A first conventional gantry frame, which is shown in FIG. 2, is relatively easy to construct and requires comparatively few materials to manufacture.

Figure 3:
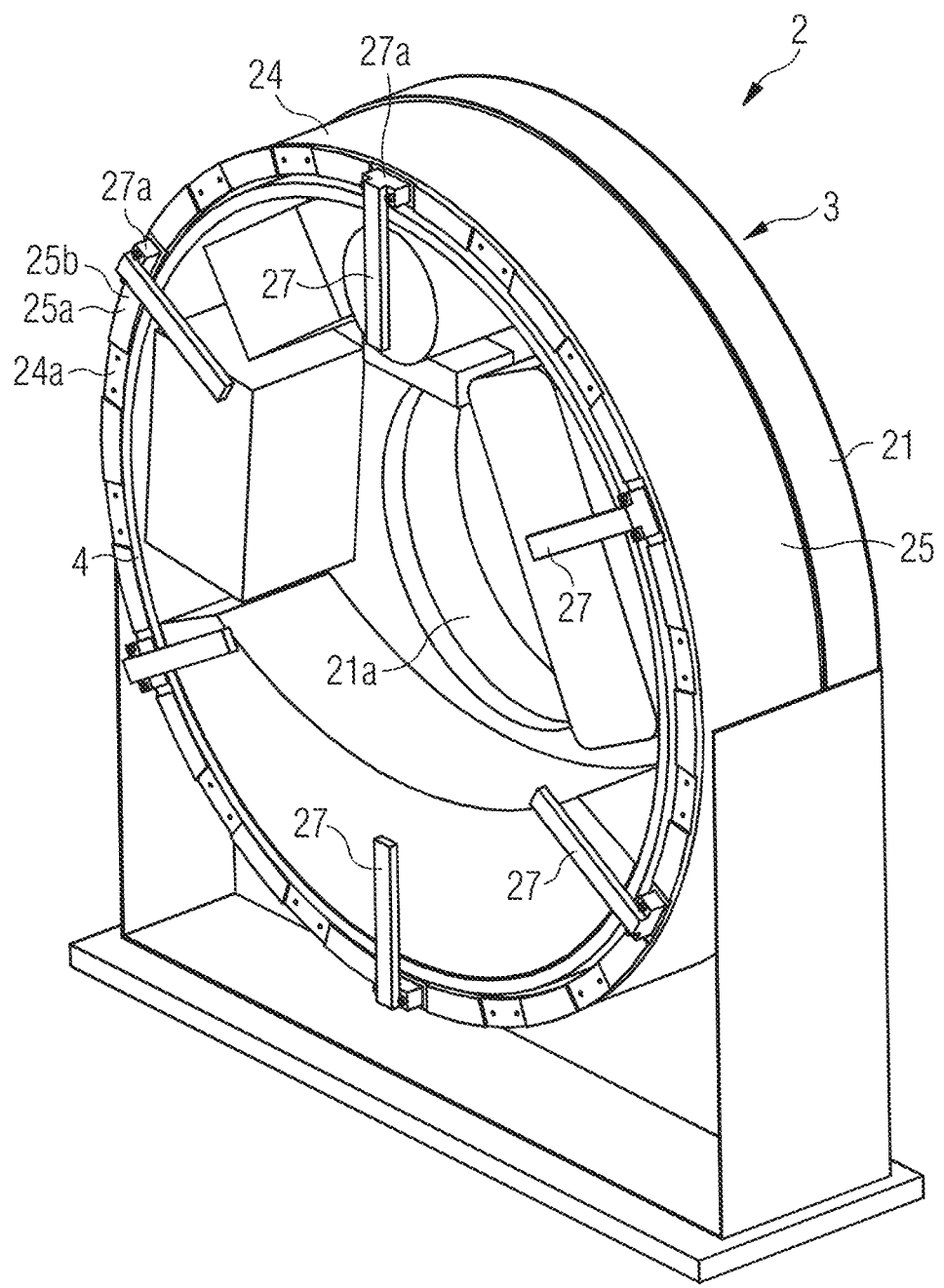
FIG. 3 shows a schematic representation of a gantry with a gantry frame with hollow chamber structures in accordance with the conventional art.

A second conventional gantry frame is shown in FIG. 3. The second conventional gantry frame has a drum frame greatly expanded in the axial direction with hollow chamber structures with an increased stability and hence improved machinability. Welding points are positioned both from inward and from outward to fasten the hollow chamber structures to a support structure.

One or more embodiments of the present invention specify a gantry frame for a computed tomography system and/or a method for manufacturing a gantry frame with an improved machinability of the gantry frame and simultaneously reduced and/or as low as possible manufacturing costs for the gantry frame.

One or more embodiments are achieved by a gantry frame for a computed tomography system, a gantry, a computed tomography system and/or a method for manufacturing a gantry frame for a computed tomography system.

A gantry frame for a computed tomography system, according to one or more embodiments, comprises a cylindrical drum frame with a cylinder barrel which has a profiled barrel structure. The drum frame serves to provide a front end surface as an attachment surface for retainers in front of the rotating part of a gantry.

A profile of a barrel structure should be understood as a location-dependent variation of the distance of the cylinder barrel from an internal and/or external sleeve cylinder, the longitudinal axis of which coincides with the longitudinal axis of the cylinder barrel. In this case the internal sleeve cylinder touches the cylinder barrel from the inside and the external sleeve cylinder touches the cylinder barrel from the outside in each case at at least one point on the internal surface or external surface of the cylinder barrel, wherein there is at least one area of the internal surface and/or the external surface of the cylinder barrel which does not touch the respective sleeve cylinder. The profiles thus penetrate the ideal cylindrical shape of the cylinder barrel, wherein apart from the variation or the profile structure the cylindrical shape of the cylinder barrel is however essentially retained. If the cylinder barrel comprises multiple walls, an analogous definition applies, with a correspondingly increased number of sleeve cylinders.

The variation in the distance of the cylinder barrel is preferably effected in the circumferential direction or as a function of an azimuth of a position on the cylinder barrel.

The profiled barrel structure of the cylinder barrel of the cylindrical drum frame has the advantage that it is mechanically particularly stable. Consequently the drum frame of the gantry frame, according to one or more embodiments, is less deformed during the machining thereof, such that the drum frame of the gantry frame can be machined more precisely. For example, assembly sections, such as for example a machinable surface for the receipt of a retainer or a fastening element for a retainer, are generated on the drum frame by milling out. During this milling out an exact position of the retainers is established. Therefore the drum frame must not deform to a relevant extent during this work step, since if it did the machining positions on the drum frame would deviate from the predetermined exact position, such that the precision of the machining would suffer as a result.

The gantry, according to one or more embodiments, has a gantry frame, an imaging system, also referred to as a rotating part, with a rotatable drum and one or more X-ray sources mounted on the drum, one or more X-ray detectors mounted on the drum, and auxiliary units, also referred to generally as rotating components. The gantry shares the advantages of the gantry frame.

The computed tomography system, according to one or more embodiments, comprises an inventive gantry. Part of the computed tomography system is also a control unit to control the gantry for a recording of X-ray raw data in accordance with an image recording protocol and an operating unit for entering control data for the control of an imaging procedure and for monitoring the imaging procedure. The computed tomography system shares the advantages of the gantry frame.

In accordance with the method for manufacturing a gantry frame for a computed tomography system, according to one or more embodiments, a cylindrical drum frame with a cylinder barrel is formed, which has a profiled barrel structure. The method for manufacturing a gantry frame for a computed tomography system shares the advantages of the gantry frame.

Further particularly advantageous embodiments and developments emerge from the following description and the figures, wherein the independent claims in one claim category can also be developed analogously to the dependent claims in a different claim category.

The profiled barrel structure preferably has a trapezoidal profile. The trapezoidal profile advantageously achieves an increased stability of the cylinder barrel of the drum frame of the gantry frame with little use of material, as a result of which a lower weight is achieved. The trapezoidal profile is advantageously formed in the axial direction, i.e. viewed in the direction of the longitudinal axis of the drum frame, wherein the trapezoidal surfaces of the trapezoids of the trapezoidal profile are oriented in parallel to the longitudinal axis of the drum frame. In other words, a normal to the trapezoidal surfaces runs parallel to the longitudinal axis. Hence where appropriate the radial dimensions, in other words the thickness of the cylinder barrel, can be reduced in comparison with conventional gantry frames with conventional hollow chamber structures. As already mentioned, with the increased stability the machinability of the gantry frame improves in comparison with conventional gantry frames. A trapezoidal profile can also be manufactured relatively easily with simple tools in comparison with other profiled, possibly more complex profile structures, as is explained below.

Likewise the cylinder barrel of the gantry frame preferably has a plurality of barrel sections, of which at least one barrel section, preferably a plurality of the barrel sections, comprises or comprise a profiled structure, preferably a trapezoidal profile, particularly preferably a double trapezoid profile. The more profiled barrel sections the barrel structure has in the circumferential direction, the greater the stability of the barrel structure because of the mechanical support effect of the profiled barrel structure. The particular advantages of a double trapezoid profile, in particular for a manufacturing process of a gantry frame, are explained fully below.

Very particularly preferably, each of the barrel sections actually has a profiled structure, preferably a trapezoidal profile and very particularly preferably a double trapezoid profile, which is concomitant with an even further improved stability of the barrel structure.

Likewise preferably, adjacent barrel sections are designed to be oriented virtually contrariwise. "Oriented virtually contrariwise" is here intended to mean that the adjacent barrel sections are approximately mirrored or are arranged rotated to one another by somewhat less or somewhat more than 180°, wherein the aforementioned deviation depends on the size of the circumference of the cylinder barrel and the extension of the individual barrel sections in the circumferential direction. In the case of a barrel section with an individual trapezoidal profile this means that the base of a trapezoidal profile and the roof side of a trapezoidal profile of adjacent barrel sections of the axis of rotation of the cylinder barrel are alternately facing one another, or the base of a trapezoidal profile of a barrel section is not so far away from this axis as the corresponding side of the trapezoidal profile of an adjacent barrel section. If the individual barrel sections each have an individual trapezoidal profile, then in the event that at least two types of barrel sections with at least one different base angle of the trapezoidal profile are selected, the barrel sections are assembled to form a cylinder barrel with a polygonal, approximately circular cross-section.

The profiles of all barrel sections of the drum frame of the gantry frame are however particularly preferably shaped identically. In this case the profile of the individual barrel sections must be designed such that their cross-sections form a circular arc after the individual barrel sections have been assembled. The barrel sections can advantageously be manufactured with an identical shape in each case with a single forming tool, as a result of which the cost of manufacturing is reduced in comparison with the manufacture of differently shaped barrel sections, for example using different forming tools.

If the individual barrel sections have an identical trapezoidal profile, the barrel sections can, as already mentioned, very particularly advantageously have a double trapezoid profile with two different (individual) trapezoidal profiles arranged so as to be oriented virtually contrarily to one another. In this case the base of a first trapezoid lies closer to the axis of rotation than the base of the second trapezoid. Furthermore, both the different trapezoidal profiles must have a different base angle, so that when the barrel sections are joined together a cylinder barrel with an approximately circular cross-section is produced. A single forming tool, such as for example a press mold or a casting mold, can advantageously be used for these shingle-like barrel sections, in order to manufacture all barrel sections, such that the outlay for manufacturing the barrel sections is reduced in comparison with manufacturing different barrel sections. Compared to manufacturing differently shaped barrel sections, the number of work processes for manufacturing the barrel sections needed for the drum frame is cut by half. The outlay when joining the individual barrel sections to form a cylinder barrel is also reduced by half because of the double cross-section width of the barrel sections in comparison with barrel sections with individual profiles of equal size.

The aforementioned variant is then advantageous in particular when the barrel sections of the cylinder barrel of the gantry frame are initially designed as individual separate barrel elements which are designed to be permanently connectable to one another using a joining technique. Individual barrel elements can then advantageously be more easily prefabricated and assembled subsequently, which for example simplifies a process based on the division of labor and reduces the space requirements for part of the manufacturing process.

The gantry frame described can be employed for a single-source CT system or a multi-source CT system. If it is used for a single-source CT system, the drum frame is arranged on one side on a supporting carrier structure, wherein the drum frame with the supporting carrier structure forms the gantry frame.

If the gantry frame is employed for what is known as a dual-source CT system or even a multi-source system in which the imaging system comprises two separate X-ray sources as well as two separate X-ray detectors opposite the respective X-ray sources and also additional auxiliary units or rotating components, the drum frame of the gantry frame has two cylindrical drum frame sections, which are referred to for short below as the first and second drum frame section. Both the drum frame sections each comprise a cylinder barrel, each of which has a profiled barrel structure. Because of the profiled barrel structure of both the cylinder barrels, both drum frame sections of the gantry frame are stabilized.

Both the drum frame sections additionally comprise two end surfaces in each case, an external and an internal end surface, of which in each case the internal end surface is connected to an end surface of a supporting carrier structure of the gantry frame arranged between both the drum frame sections. The external end surface of both the drum frame sections is in contrast oriented outward, in other words facing away from the supporting carrier structure. The carrier structure forms the supporting central element of the gantry frame, absorbs forces onto the gantry frame and stabilizes the entire gantry. The carrier structure preferably has a box profile. Thanks to the formation of a box profile the carrier structure becomes stable and in comparison with a solid construction the weight of the carrier structure is reduced and material is saved.

At least some of the additional auxiliary units or rotating components can advantageously be accommodated in a second drum, which is surrounded by the second drum frame section, if there is no space for it in a first drum, which is surrounded by the first drum frame section, since a larger number of units has to be accommodated there than in the case of a single-source CT system.

In this advantageous embodiment both the drums received by the drum frame extend the gantry preferably in an axial direction beyond the carrier structure in comparison with a single-source CT system, wherein the second drum is formed on the rear side of the carrier structure. In this way additional capacities for auxiliary units of a dual-source system or multi-source system are created, without increasing the clearance profile of the gantry frame, such that transportation through constricted openings, such as door frames or portals for example, is facilitated.

The drum frame or at least one of the cylindrical drum frame sections of the gantry frame preferably has a machined surface and/or a fastening element for the receipt of a retainer for extension elements at its external end surface, which faces away from the carrier structure. The extension elements serve among other things to enable a user or an operator of such a gantry to operate the associated computed tomography system with ease or to provide easy access to the operation. Peripheral units of the gantry of the gantry frame can advantageously be connected to the drum frame or the drum frame section and can be arranged and positioned particularly accurately on the end face of the gantry frame because of the increased precision of the structures of the machined surface or of the fastening element.

The extension elements of the gantry frame preferably have at least one of the following elements:
a control panel,
a display,
a protective enclosure,
a front cover,
a laser.

The precision of the arrangement of the retainers is particularly important, since functional units that are mounted on the retainers are allotted an accurate positioning in order to function correctly. For example, a laser is required in order to produce a fixed reference to the scanning plane when recording an image of a patient and to establish a scanning area. In the case of a biopsy, positions are established by a laser. It is crucial here for the health of a patient and the success of the biopsy that the desired body position is hit accurately. The positioning of a cover, also called a front cover, must also be precise, so that the cover is tight and for example none of the patient's bodily fluids can flow into the interior of the gantry. When closed, the front cover must also adopt a particularly precise position, so that it can be automatically determined whether the front cover is closed or open.

Particularly preferably the profiled barrel structure has a single-wall barrel structure. The barrel structure is advantageously simpler in structure in comparison with multi-wall barrel structures, for example barrel structures with hollow chamber structures, requires less material and weighs less. A gantry frame with a single-wall barrel structure is also easier to assemble and manufacture in comparison with a gantry frame with a hollow chamber structure, this being described more fully below in connection with a variant of the manufacturing method of the gantry frame.

Additional advantages emerge in particular with this particularly preferred variant of the method, in which individual barrel sections are initially formed as separate elements. This procedure can for example take place by a forming method, such as for example a pressing method or a stamping method, in which the individual barrel sections are formed from pre-cut metal sheets. By pressing the metal sheets, the barrel sections attain the desired profiled structure. The metal sheets can for example comprise steel as a material.

The prefabricated individual barrel sections are then connected to an end surface of a carrier structure. In this case they can for example be welded to the end surface of the carrier structure. For this procedure the individual barrel sections are positioned and oriented to one another and preferably joined to one another or joined into one another in a shingle-like or overlapping manner and preferably also welded, such that they form the cylinder barrel of the drum frame. The barrel sections can advantageously be initially prefabricated in a space-saving manner using simple tools and later assembled at the location of the final installation of the gantry frame.

If the profiled barrel structure is designed as a single-wall barrel structure, work steps for the manufacture of the gantry frame can advantageously be saved, in particular in comparison with the manufacture of a gantry frame with a hollow chamber structure. For example, the accessibility of the welding points is improved in comparison with a hollow chamber structure when the barrel sections are fastened to the carrier structure by welding. Then, in contrast to the fastening of barrel sections with hollow chamber structures, a welding device need be applied only from one side, for example from outside, when single-wall barrel sections are used, such that the installation of the barrel sections on the carrier structure is simplified.

Fastening elements can then be attached to one or more end surfaces of barrel sections fastened to the carrier structure in this way, or retainers can be attached directly. To this end the external end surfaces of the barrel sections in question can be appropriately pretreated. For example, recesses or projections can be formed in the external end surfaces, to which the fastening elements or retainers can then be attached. In an additional machining step the fastening elements can then be machined, preferably milled, such that they attain their final shape and are prepared for the receipt of retainers in the correct position for the previously mentioned extension elements.

FIG. 1 shows a general schematic representation of a computed tomography system 1, in order to illustrate its general structure. The arrangement comprises a gantry 2 with a stationary part 3, also referred to as a gantry frame, and with a part 4a rotatable or rotating about a system axis 5, said part 4a having a drum 4. The rotating part 4a, which has the function of an imaging system (X-ray system) 4a, comprises not only the drum but also an X-ray source 6 and an X-ray detector 7, which are arranged in the drum 4 opposite to one another. The X-ray source 6 and X-ray detector 7 together with the drum 4 form the imaging system 4a. During operation of the computed tomography system 1 X-ray radiation 8 is emitted from the X-ray source 6 toward the X-ray detector 7, penetrates a scanning object P, for example a patient P, and is detected by the X-ray detector 7 in the form of measured data or measured signals.

FIG. 1 further shows a patient couch 9 for positioning a patient P. The patient couch 9 comprises a couch base 10, on which is arranged a patient positioning plate 11 provided for the actual positioning of the patient P. The patient positioning plate 11 can be adjusted relative to the couch base 10 in the direction of the system axis 5, such that it can be introduced, together with the patient P, into an opening 12 or into the patient receiving area 12 of the gantry 2 to enable X-ray projections of the patient P to be taken. The computational processing of the X-ray projections taken with the imaging system 4a or the reconstruction of slice images, 3D images or of a 3D dataset based on the measured data or measured signals of the imaging system 4a is effected with an image processor 13 of the computed tomography system 1, wherein the slice images or 3D images can be represented on a display device 14. The image processor 13 can also be designed as a control device for controlling an imaging process to control the gantry 2 and in particular the imaging system 4a.

So that the rotating part 4a forming the imaging system 4a can rotate relative to the stationary part 3 of the gantry 2, it is necessary for the rotating part 4a to have a bearing arrangement. To this end an annular roller bearing is used for example, which is arranged axially in approximately the center of the gantry 2 and moves annularly around the patient receiving area 12.

FIG. 2 shows a gantry 2 with a conventional gantry frame 3 with support arms 22. The gantry frame 3 comprises a supporting carrier structure 21 on the back of the gantry frame 3. The carrier structure 21 is designed to be relatively narrow in the axial direction, but in the radial direction it has a large diameter to receive a cylindrical drum 4. Arranged on the external sides of the carrier structure 21 are a plurality of support arms 22 which run in the axial direction and project out over the drum 4. What are known as retainers 27 are fastened to the support arms 22 and run at an angle of 90° to the support arms 22 or radially to the axis of rotation of the drum 4. Functional elements, such as for example a control panel, a display and similar units (not shown) can be fastened to the retainers 27 and should be accessible from the front of the gantry 2.

FIG. 3 shows a second gantry 2 with a conventional gantry frame 3 with a drum frame 24, greatly extended in the axial direction, with hollow chamber structures 25b with increased stability. In this case the drum frame 24 in the representation in FIG. 3 extends left from a carrier structure 21 with an annular bearing 21a, in which a drum 4 is rotatably mounted. The drum frame 24 has a cylinder barrel 25 with individual segments or barrel sections 25a with the aforementioned hollow chamber structures 25b which together form the cylinder barrel 25 of the drum frame 24. The hollow chamber structures 25b increase the stability of the gantry frame 3. Attached to the end face 24a of the drum frame 24 are retainers 27 running in the radial direction. The retainers 27 are fastened with fastening elements 27a to the end face 24a of the drum frame 24. The fastening elements 27a are welded to the end face 24a and have been manufactured by milling. Extension elements, such as for example what is known as a front cover (not shown) can be mounted on the retainers 27.

Figure 4:
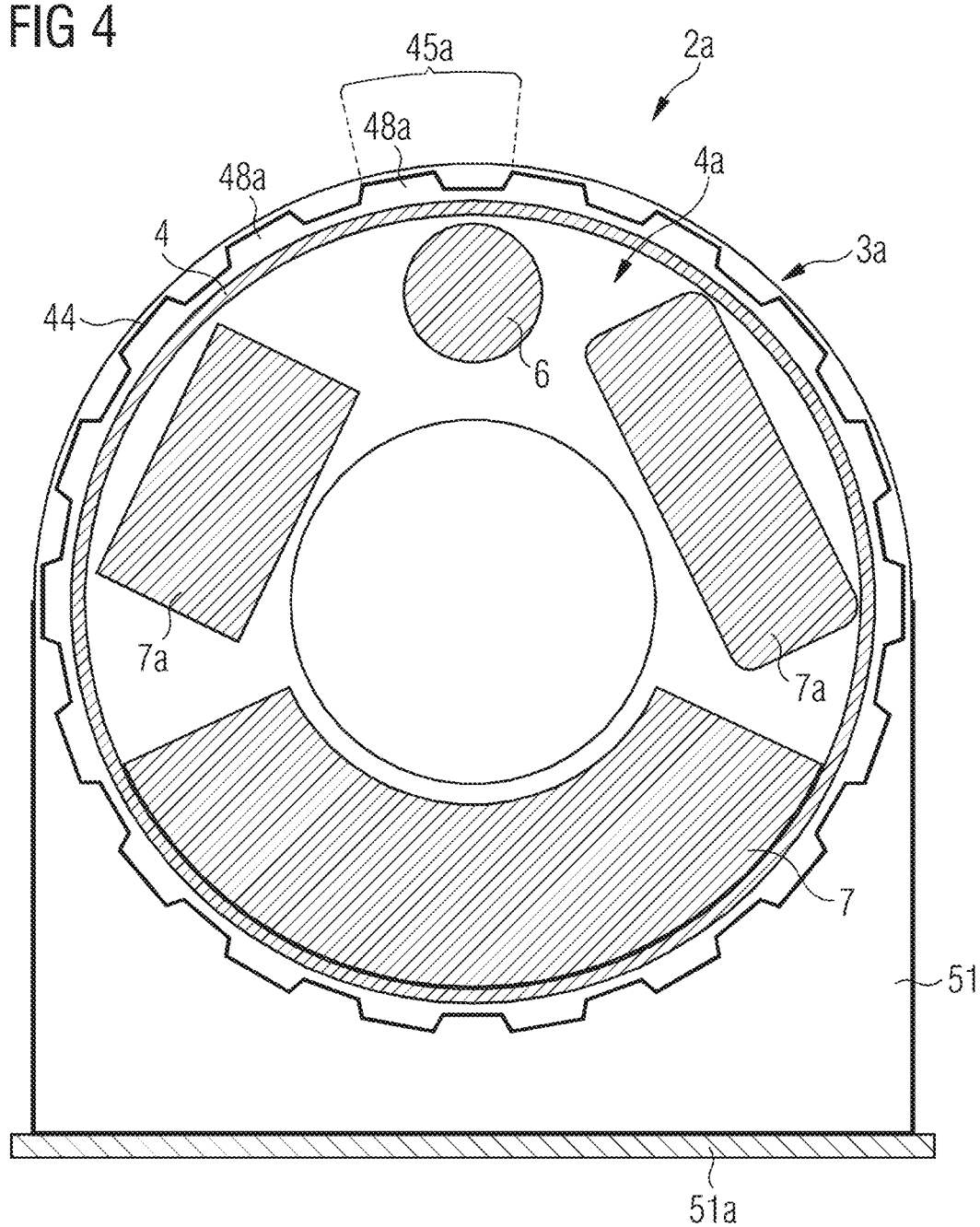
FIG. 4 shows a front sectional view of a gantry with a gantry frame in accordance with a first exemplary embodiment of the invention.

FIG. 4 shows a sectional view of a gantry 2a with a gantry frame 3a in accordance with a first exemplary embodiment of the invention viewed from the front. The gantry frame 3a is designed for what is known as a single-source CT system. In this case the components 6, 7, 7a of the imaging system 4a, in other words both the X-ray source 6 and the X-ray detector 7 as well as the other rotating components 7a, are located in one and the same drum 4 and are hatched because of the sectional view. Because of the restriction to a single X-ray source 6 and a corresponding X-ray detector 7 the space is sufficient for just a single drum, meaning that for a single-source CT system only a single drum 4 is required. The drum 4 is rotatably mounted in a rotation bearing 21a (see FIG. 5) and is surrounded by a stationary drum frame 44, which is fastened to a carrier structure 41 (see FIG. 5). The drum frame 44 comprises a plurality of barrel sections 45a, each of which has a single-wall trapezoidal profile designed as a double trapezoid profile 48a. In the lower part of FIG. 4 a support structure 51 of the gantry frame 3a with a supporting box profile and a base plate 51a can also be seen, on which the support structure 51 is constructed.

Figure 5:
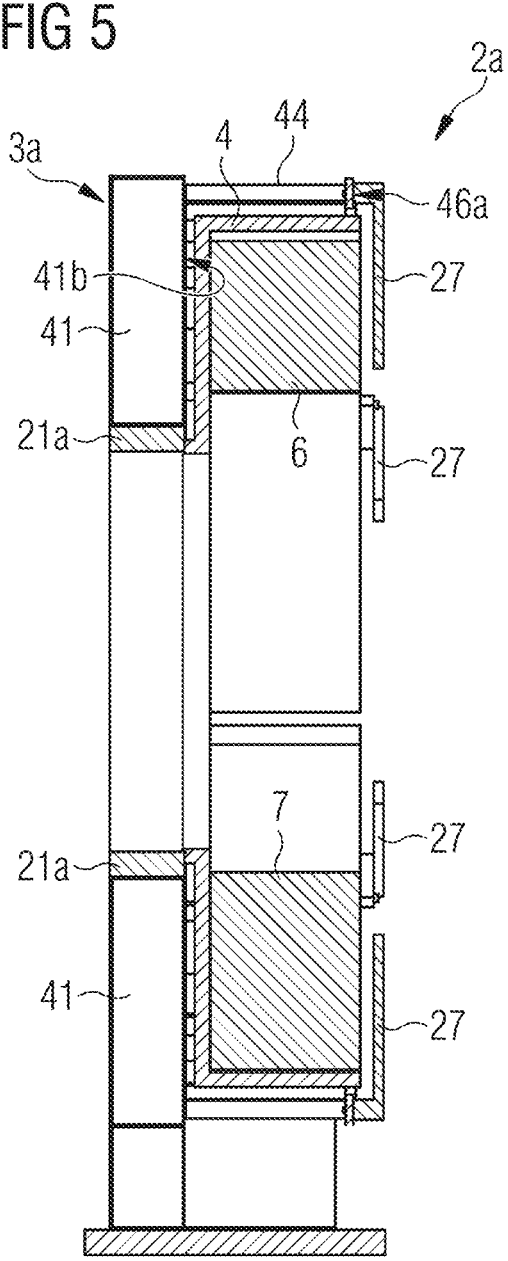
FIG. 5 shows a lateral sectional view of the gantry shown in FIG. 4.

FIG. 5 schematically represents a sectional view of the gantry 2a shown in FIG. 4 with the gantry frame 3a viewed from the side. It is likewise also apparent in FIG. 5 that the drum frame 44, the uppermost section of which is shown at the very top in the representation in FIG. 5, has a single-wall barrel structure. Because of the double trapezoid profile 48a of the drum frame 44, which can be seen in FIG. 4 and FIG. 6, the single-wall drum frame 44 is very stable. FIG. 5 shows, once again hatched, the X-ray source 6 and the X-ray detector 7 inside the drum 4, since they are cut open in the representation shown in FIG. 5. Retainers 27 are also drawn in on the front of the drum frame 44 in FIG. 5, and are attached to a front end surface 46a of the drum frame 44. The aforementioned carrier structure 41 in box profile form can also be seen on the left, and surrounds the likewise aforementioned rotation bearing 21a of the gantry frame 3a, in which the drum 4 is mounted. It is also apparent in the lateral view in FIG. 5 that the drum frame 44 is fastened to a first front end surface 41b of the carrier structure 41.

Figure 6:
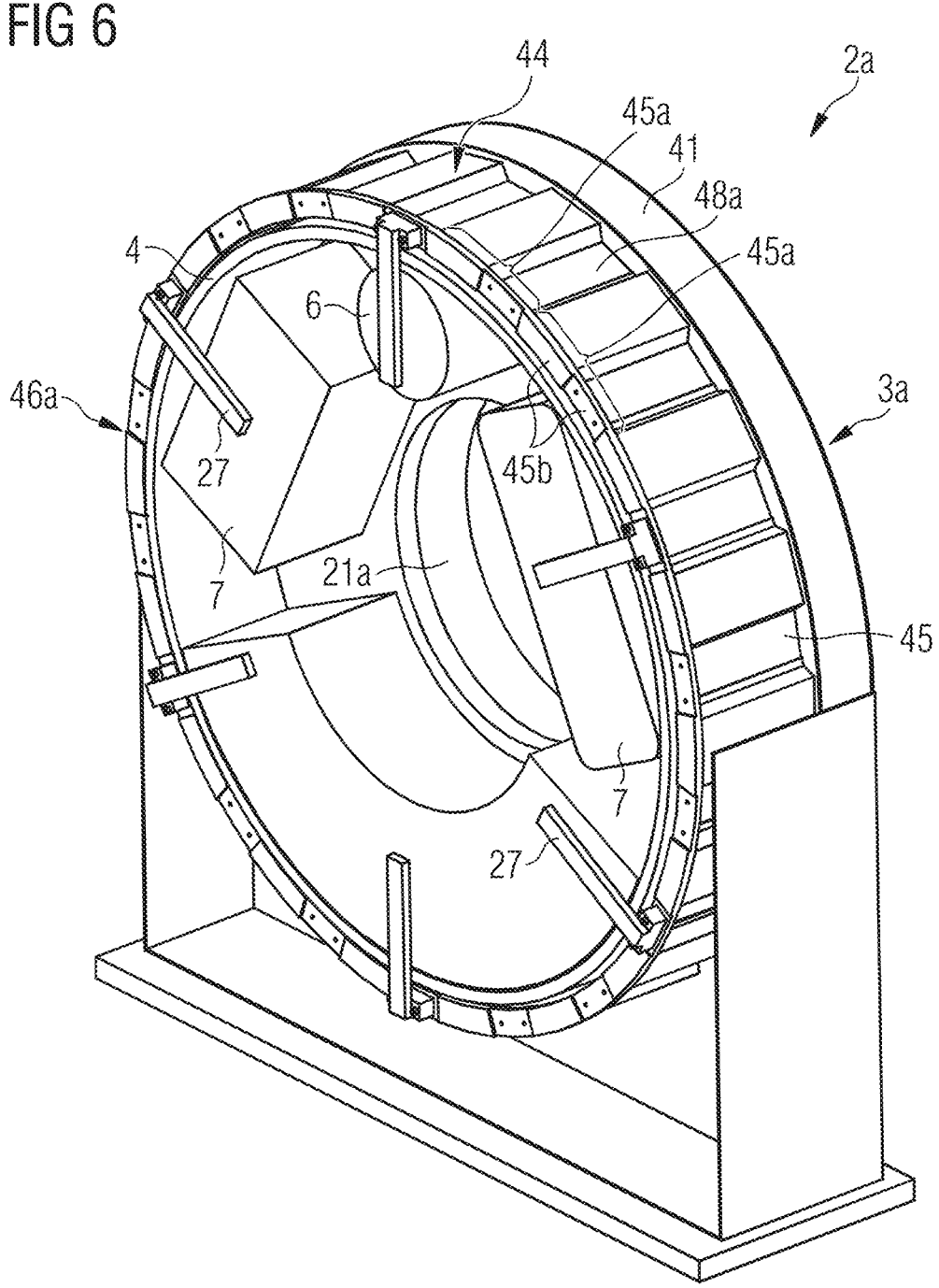
FIG. 6 shows a schematic perspective view of the gantry shown in FIG. 4 and FIG. 5 viewed obliquely from the front.

FIG. 6 shows a schematic perspective view of the gantry 2a shown in FIG. 4 and FIG. 5 viewed obliquely from the front. From this perspective the profiling of the cylinder barrel 45 of the drum frame 44 with its individual barrel sections 45a is particularly readily apparent. As already mentioned, the individual barrel sections 45a have a double trapezoid profile 48a and are in each case formed in the manner of shingles or steps. The double trapezoid profile 48a of an individual barrel section 45a in each case has two trapezoidal end surfaces 45b, of which in each case the base of one of the two trapezoidal end surfaces 45b lies closer to the drum 4 and the base of the other of the two trapezoidal end surfaces 45b lies further away from the drum 4. The barrel sections 45a in each case form a segment or element of the cylinder barrel 45 of the drum frame 44. Together the end surfaces 45b of the barrel sections 45a form the front end surface 46a of the drum frame 44. Fastened to the front end surface 46b of the drum frame 44 are retainers 27 extending in the radial direction, which can support extension elements (not shown). As already mentioned, the drum 4 is mounted in a rotation bearing 21a, which can be identified in FIG. 6 from a perspective view, in the rear area of the gantry frame 3a, which is formed by a carrier structure 41 with a box profile form. Despite the embodiment with a single-wall cylinder barrel 45 the drum frame 44 is very stable, because the double trapezoid profile 48a of the cylinder barrel 45 brings with it a mechanical strengthening.

Figure 7:
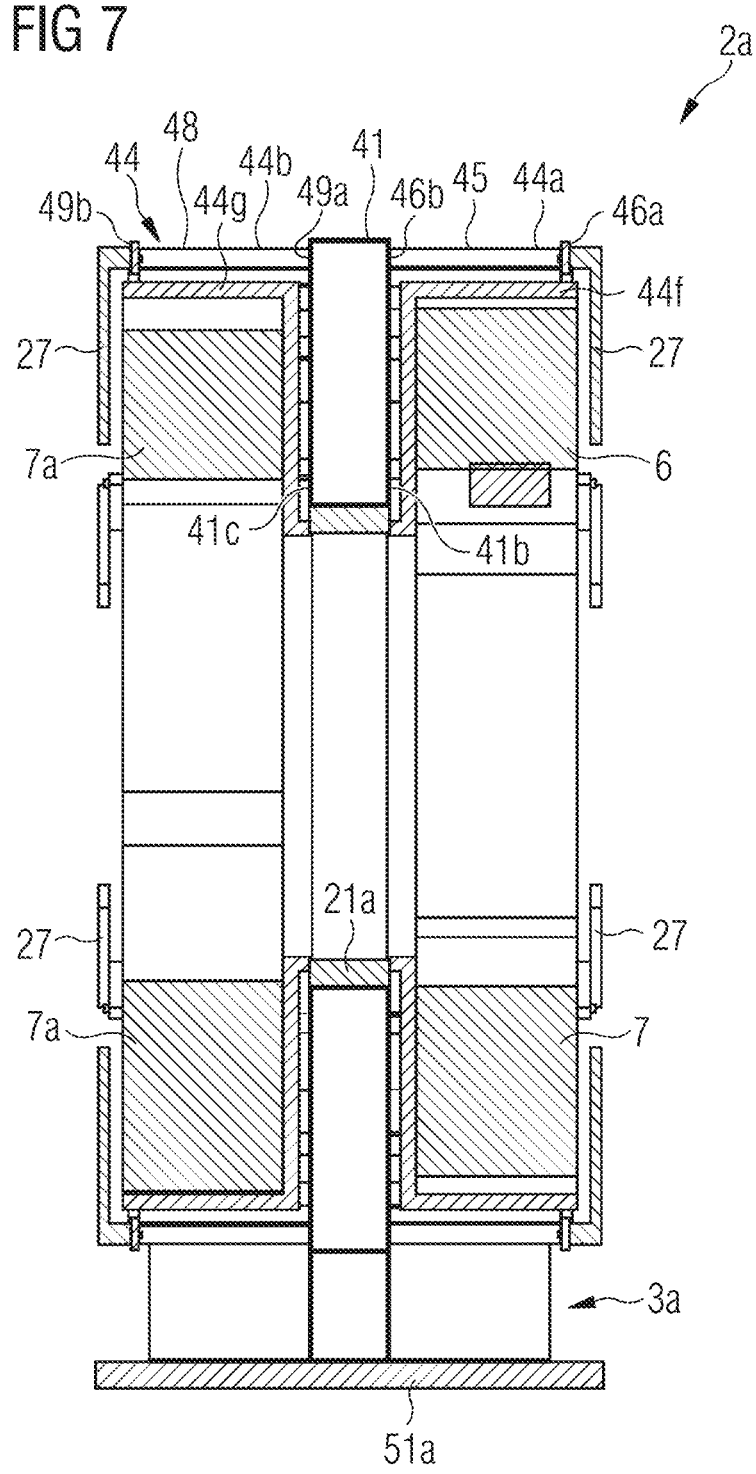
FIG. 7 shows a schematic lateral sectional view of a gantry with a gantry frame in accordance with a second exemplary embodiment of the invention.
Figure 8:
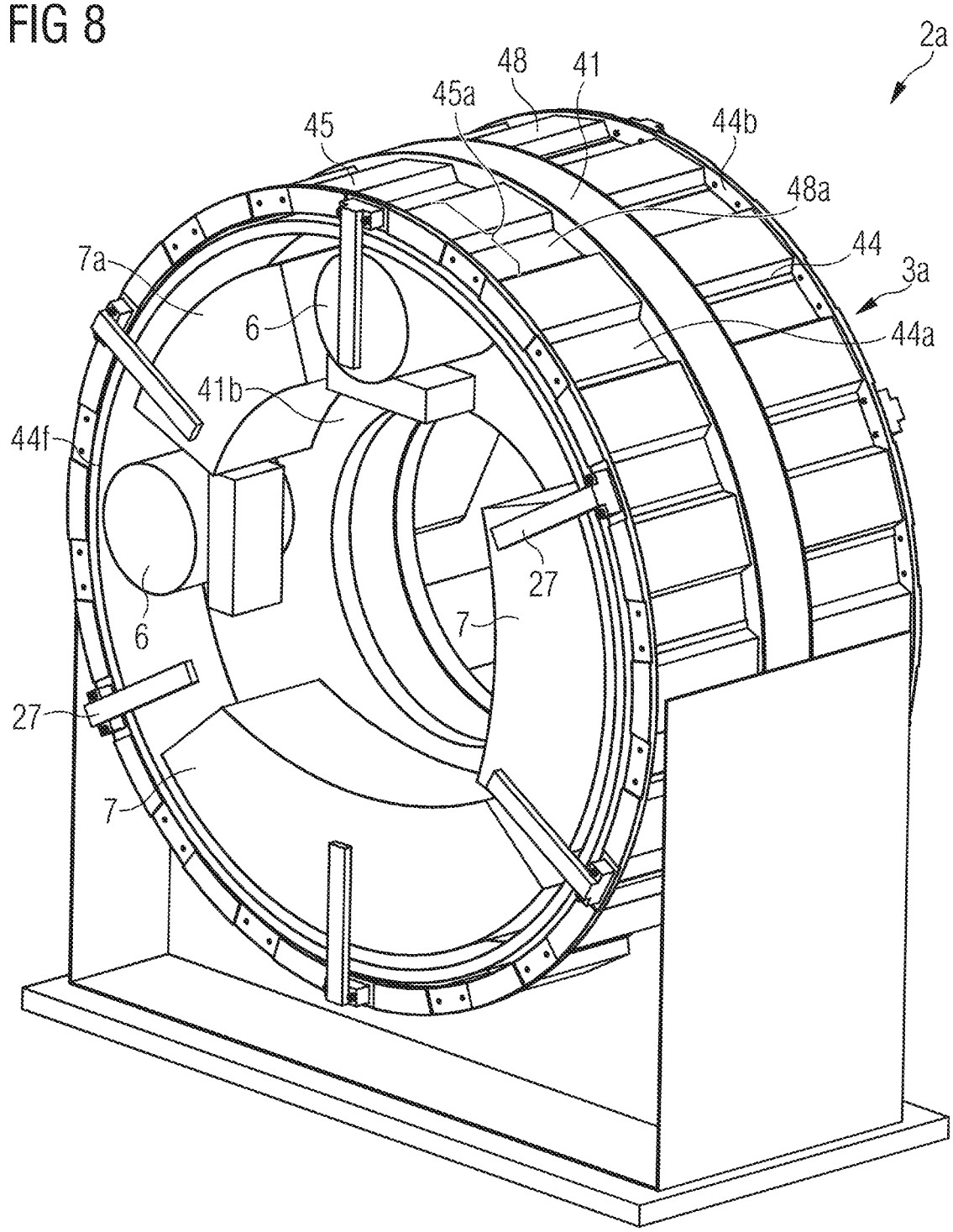
FIG. 8 shows a schematic perspective view of the gantry shown in FIG. 7 viewed obliquely from the front.

FIG. 7 and FIG. 8 show schematic representations of a gantry 2a with a gantry frame 3a in accordance with a second exemplary embodiment of the invention. The gantry frame 3a shown in FIG. 7 and FIG. 8 is designed for what is known as a dual-source CT system. In this case both two X-ray sources 6 and two X-ray detectors 7 as well as an additional rotating component 7a, such as for example an electronics box, are located in a front drum section 44f (see the right-hand half of FIG. 7) of the drum 4 and further rotating components 7a are located in a rear drum section 44g of the drum (see the left-hand half of FIG. 7). A front drum section 44f should here be understood as the section of the drum 4 in which an image recording by the X-ray sources 6 and X-ray detectors 7 arranged there also takes place.

Similarly to the conventional gantry frame 3 in FIG. 3 the gantry frame 3a in accordance with a second exemplary embodiment of the invention in FIG. 7 and FIG. 8 has a greatly extended structure of a drum frame 44 in the axial direction with two drum frame sections 44a, 44b. The drum frame sections 44a, 44b are arranged in the axial direction on both sides of a centrally positioned carrier structure 41 and form a wide drum frame 44 which can receive two drums 44f, 44g arranged one behind the other in the axial direction which are screwed to a bearing 21a which is part of the carrier structure 41. A front drum 44f is screwed to the bearing 21a from the front and a rear drum 44g is screwed to the bearing 21a from the rear. The carrier structure 41 has a first end surface 41b as a front end surface and a second end surface 41c as a rear end surface. Both the drum frame sections 44a, 44b are in each case fastened to one of the two end surfaces 41b, 41c of the carrier structure 41. The two drum frame sections 44a, 44b do not, unlike in the drum frame 24 shown in FIG. 3, have a cylinder barrel with hollow chamber structures 25b, but in each case a single-wall cylinder barrel 45, 48, i.e. a first cylinder barrel 45 and a second cylinder barrel 48 axially offset thereto, with double trapezoid profiles 48a (see FIG. 8).

The two cylinder barrels 45, 48, which are shown foreshortened in FIG. 8, are, analogously to the first form of embodiment shown in FIG. 4 to FIG. 6, formed with a plurality of barrel sections 45a with the aforementioned double trapezoid profiles 48a abutting one another in the circumferential direction, wherein the structure of the double trapezoid profiles 48a is apparent from the perspective selected in FIG. 8.

FIG. 7 shows a schematic sectional view of the gantry 2a with a gantry frame 3a in accordance with a second exemplary embodiment viewed from the side. The right-hand half of FIG. 7 shows in a hatched manner the front drum 44f with the aforementioned distribution of the components 6, 7 for imaging, since it is cut by the sectional plan selected in FIG. 7. A first X-ray source 6 is located in the upper area of the front drum 44f and a first X-ray detector 7 can be seen in the lower area of the front drum 44f, in other words the area toward the base plate 51a. Further shown hatched in FIG. 7 in the rear drum 44g, which is shown in the left-hand half of FIG. 7, are auxiliary units or rotating components 7a. Also once again drawn in in FIG. 7 are several retainers 27 on both the end faces of the drum frame 44, which are fastened to the external end surfaces 46a, 49b of the drum frame 44. In this case the front external end surface 46a is also referred to as the first external end surface 46a and the rear external end surface 49b is also referred to as the second external end surface 49b. Also shown in FIG. 7 are both the internal end surfaces 46b, 49a, i.e. the rear end surface 46b of the first drum frame section 44a, also referred to as the first internal end surface 46b, and the front end surface 49a of the second drum frame section 44b, also referred to as the second internal end surface 49a, with which both these drum frame sections 44a, 44b are fastened to the end surfaces 41b, 41c of the central carrier structure 41. Reference is made to the shared description of FIG. 7 and FIG. 8 above in respect of further features shown in FIG. 7.

FIG. 8 shows a schematic perspective view of the gantry 2a shown in FIG. 7 with a gantry frame 3a in accordance with a second exemplary embodiment of the invention viewed obliquely from the front. From this perspective the drum frame 44 with its double trapezoid profile 48a embodied as a double frame can be particularly easily identified. The drum frame 44 comprises two drum frame sections 44a, 44b, embodied analogously to the drum frame 44 of the gantry frame 2a in accordance with the first exemplary embodiment (see FIG. 4 to FIG. 6), with in each case a cylinder barrel 45, 48 with a plurality of barrel sections 45a with the double trapezoid profile 48a already fully explained in connection with FIG. 4 to FIG. 6. Fastened to the first external end surface 46a are six retainers 27 arranged at a 60° angle to one another, which can be used to fasten the aforementioned extension elements to the drum frame 44.

Reference is made to the shared description of FIG. 7 and FIG. 8 above in respect of further features shown in FIG. 8.

FIG. 9 shows a flow diagram 900 which illustrates a method for manufacturing a gantry frame in accordance with an exemplary embodiment of the invention. A cylindrical drum frame 44 with a single-wall cylinder barrel 45 with a trapezoidal profile is embodied in the context of the method.

In step 9.I individual barrel sections 45a are initially stamped from pre-cut metal sheets by a pressing method, wherein thanks to the metal sheets being pressed they obtain a trapezoidal profile, in particular a double trapezoid profile with trapezoidal end surfaces. In step 9.II a carrier structure 41 in box profile form is manufactured. The carrier structure 41 is mounted on a base plate 51a together with a support structure 51 for the gantry frame 3a. Then in step 9.III the individual barrel sections 45a are arranged on a first end surface 41b of the carrier structure 41, for example via a plug-in connection, and are connected to one another by their nested profile shape. In this case they are in each case joined to one another, such that they form the cylinder barrel 45 of the drum frame 44. The barrel sections 45a are then welded to one another and the barrel sections 45a are welded to the carrier structure 41. In step 9.IV fastening elements 27a for receiving retainers 27 are welded onto several end surfaces 45b of the barrel sections 45a. These fastening elements 27a are finally milled in step 9.V, such that they attain their final shape and an accurate positioning and are prepared for the receipt of the retainers 27.

Finally it is pointed out once again that the gantries or gantry frames described in detail above relate merely to exemplary embodiments which can be modified in a variety of ways by the person skilled in the art, without departing from the scope of the embodiments of the invention. Furthermore, the use of the indefinite article "a" or "an" does not rule out that the features in question may also be present multiple times. Likewise the term "unit" does not rule out that the component in question may consist of multiple interworking subcomponents which where appropriate may also be spatially distributed.

What is claimed is:

1. A gantry frame for a computed tomography system, the gantry frame comprising:
a cylindrical drum frame with at least one cylinder barrel, the at least one cylinder barrel having a profiled barrel structure and a plurality of barrel sections, at least one barrel section, among the plurality of barrel sections, having a profiled structure,
wherein the plurality of barrel sections are designed as individual barrel elements, the individual barrel elements configured to be permanently connectable to one another by a joining technique.

2. The gantry frame as claimed in claim 1, wherein the profiled barrel structure has a trapezoidal profile.

3. The gantry frame as claimed in claim 1, wherein the plurality of barrel sections have profiled structures.

4. The gantry frame as claimed in claim 1, wherein the profiled structure comprises a double trapezoid profile.

5. The gantry frame as claimed in claim 1, wherein adjacent barrel sections of the at least one cylinder barrel are configured to be oriented contrariwise to one another.

6. The gantry frame as claimed in claim 1, wherein profiles of all barrel sections of the at least one cylinder barrel are identical in shape.

7. The gantry frame as claimed in claim 1, wherein
the cylindrical drum frame has at least two cylindrical drum frame sections,
each of the at least two cylindrical drum frame sections includes a respective cylinder barrel, each respective cylinder barrel having the profiled barrel structure, and
each of the at least two cylindrical drum frame sections includes two end surfaces, an external end surface, and an internal end surface, of which in each case the internal end surface is connected to an end surface of a carrier structure of the gantry frame arranged between the at least two cylindrical drum frame sections.

8. The gantry frame as claimed in claim 1, wherein the profiled barrel structure comprises a single-wall barrel structure.

9. A gantry, having:
the gantry frame as claimed in claim 1, and
a rotating part with a function of an imaging system.

10. The gantry frame as claimed in claim 1, wherein at least one barrel section, among the plurality of barrel sections, has a trapezoidal profile.

11. The gantry frame as claimed in claim 2, wherein adjacent barrel sections of the at least one cylinder barrel are configured to be oriented contrariwise to one another.

12. The gantry frame as claimed in claim 4, wherein profiles of all barrel sections of the at least one cylinder barrel are identical in shape.

13. The gantry frame as claimed in claim 5, wherein each of the plurality of barrel sections has a profiled structure.

14. The gantry frame as claimed in claim 7, wherein the cylindrical drum frame or at least one of the at least two cylindrical drum frame sections has a machined surface configured to receive a retainer for extension elements on the external end surface.

15. A computed tomography system, comprising:
the gantry as claimed in claim 9,
at least one processor configured to execute computer-executable instructions to
control the gantry to receive X-ray raw data in accordance with an image recording protocol,
receive control data for control of an imaging procedure, and
monitor the imaging procedure.

16. The gantry frame as claimed in claim 13, wherein the profiled structure comprises a double trapezoid profile.

17. A method for manufacturing a gantry frame for a computed tomography system, the method comprising:
forming a cylindrical drum frame having a cylinder barrel, the cylinder barrel having a profiled barrel structure;
forming individual barrel sections with a profiled barrel section structure as separate elements; and
connecting the individual barrel sections to an end surface of carrier structure, such that the individual barrel sections form the cylinder barrel of the cylindrical drum frame.

* * * * *